United States Patent
Sanchez et al.

(10) Patent No.: US 12,422,442 B2
(45) Date of Patent: Sep. 23, 2025

(54) MARKERS AND THEIR USE IN BRAIN INJURY

(71) Applicants: UNIVERSITE DE GENEVE, Geneva (CH); FUNDACIÓ HOSPITAL UNIVERSITARI VALL D'HEBRON—INSTITUT DE RECERA, Barcelona (ES)

(72) Inventors: Jean-Charles Sanchez, Geneva (CH); Joan Montaner, Barcelona (ES)

(73) Assignees: UNIVERSITE DE GENEVE, Geneva (CH); FUNDACIÓ HOSPITAL UNIVERSITARI VALL D'HEBRON—INSTITUT DE RECERCA, Barcelona (ES)

( * ) Notice: Subject to any disclaimer, the term of this patent is extended or adjusted under 35 U.S.C. 154(b) by 900 days.

(21) Appl. No.: 17/560,297

(22) Filed: Dec. 23, 2021

(65) Prior Publication Data
US 2022/0137072 A1 May 5, 2022

Related U.S. Application Data

(60) Continuation-in-part of application No. 16/698,363, filed on Nov. 27, 2019, now abandoned, which is a division of application No. 15/516,543, filed as application No. PCT/EP2015/001946 on Oct. 5, 2015, now abandoned.

(30) Foreign Application Priority Data

Oct. 6, 2014 (EP) .................................. 14003422
Aug. 19, 2015 (EP) .................................. 15002459

(51) Int. Cl.
*G01N 33/68* (2006.01)

(52) U.S. Cl.
CPC ..... *G01N 33/6896* (2013.01); *G01N 2333/47* (2013.01); *G01N 2333/4727* (2013.01); *G01N 2333/521* (2013.01); *G01N 2333/70503* (2013.01); *G01N 2333/775* (2013.01); *G01N 2333/902* (2013.01); *G01N 2333/91091* (2013.01); *G01N 2333/91177* (2013.01); *G01N 2800/28* (2013.01); *G01N 2800/60* (2013.01)

(58) Field of Classification Search
CPC ........... G01N 33/6896; G01N 2333/47; G01N 2333/4727; G01N 2333/521; G01N 2333/70503; G01N 2333/775; G01N 2333/902; G01N 2333/91091; G01N 33/54387; G01N 2333/91177; G01N 2800/28; G01N 2800/60; G01N 2333/71; G01N 2800/2871; G01N 2800/52; A61P 25/00; A61P 29/00
See application file for complete search history.

(56) References Cited

U.S. PATENT DOCUMENTS

7,955,804 B2 * 6/2011 Hochstrasser .......... A61P 21/02
435/7.1

FOREIGN PATENT DOCUMENTS

WO 2006047417 A2 5/2006
WO 2012051519 A2 4/2012

OTHER PUBLICATIONS

Notice of Acceptance of Australian Patent Application No. 2015330355, Sep. 13, 2021, 4 pages.

* cited by examiner

*Primary Examiner* — Olga N Chernyshev
(74) *Attorney, Agent, or Firm* — Synergy IP Group AG; Lily Ackerman (57) ABSTRACT

The invention relates to a combination of biomarkers and their use in brain injury or mild traumatic brain injury (mTBI) detection. The invention also relates to methods of treating the individual diagnosed with a traumatic brain injury (TBI) or a mild traumatic brain injury (mTBI) using such biomarkers.

8 Claims, 10 Drawing Sheets

For 100% sensitivity in the full cohort of patients
S100B vs. 2 markers

S100B specificity 37%

S100B+NDKA specificity 49%

For 95-100% sensitivity in the full cohort of patients
S100B vs. 2 markers

S100B specificity 37%       S100B+HFABP specificity 52%

FIG. 4

For 95-100% sensitivity in the full cohort of patients
S100B vs. 2 markers + Age

S100B specificity 37%   S100B+GSTP+Age specificity 64%

MARKERS AND THEIR USE IN BRAIN INJURY

CROSS REFERENCE TO RELATED APPLICATIONS

The present application is a continuation-in-part of U.S. application Ser. No. 16/698,363, filed Nov. 27, 2019, which is a divisional of U.S. application Ser. No. 15/516,543, filed Apr. 3, 2017, as a national phase application under 35 U.S.C. § 371 of PCT International Application No. PCT/EP2015/001946, filed Oct. 5, 2015, which claims priority to and the benefit of European Application No. 15002459.4, filed Aug. 19, 2015, and European Application No. 14003422.4, filed Oct. 6, 2014, all of which are hereby incorporated herein by reference in their entireties.

FIELD OF THE INVENTION

The invention relates to biomarkers and novel biomarkers, their use in diagnostics of brain injury or brain related injuries, in particular mild traumatic brain injury (mTBI), and methods as well as devices for the detection of same in an individual. The invention also relates to methods of treating the individual diagnosed with a traumatic brain injury (TBI) or a mild traumatic brain injury (mTBI) using such biomarkers.

BACKGROUND OF THE INVENTION

Brain injuries have a high incidence worldwide. In particular mild traumatic brain injury (mTBI) has a significant incidence in the world and is responsible for high health cost. In contrast to severe TBI, mTBI is not obvious to detect and thus usually a computer tomography (CT) scan is performed before significant brain injury can be ruled in or out.

So far, it is still a challenge identifying which patients with a number of neurological injuries and in particular a mild traumatic brain injury (mTBI), can be safely sent home. Computer tomography (CT) scan is thus the main tool today to detect a cerebral lesion in these patients. However, many of the scans are negative and cost-intense. Therefore, in any clinical decision rules for mild TBI, defined as presenting with a Glasgow Coma Score (GCS) (Jennet and Teasdale, check, 1978) of 13-15, rapid and reliable identification of patients with intracranial lesions is critical to avoid post-traumatic complications and minimize secondary brain damages (Graham, et al., 1998). Several studies aimed to first screen all mild TBI-patients with a simple blood test to reduce the number of unnecessary CT scans and discharge patients faster have been reported (Berger et al., 2007; Poli-de-Figueiredo et al., 2006). In the last years, especially S100B was extensively investigated as potential promising marker for mTBI and is highly promoted by companies. Nevertheless, its clinical utility remains controversial. In mild TBI adults, S100B below a cut-off of 0.10 pg/L was described to allow a maximal reduction of only 30% in CT scans. S100B failed to be a relevant prognostic marker for paediatric TBI patients, estimated only as adjunct in determining children with low-risk TBI (Tavarez et al., 2012).

A mild traumatic brain injury (mTBI, also called concussion, minor head trauma, and minor brain/head injury) is a type of closed head injury, defined as the result of a blunt trauma or acceleration/deceleration forces causing a brief change in mental status (confusion, disorientation or loss of memory) or loss of consciousness for less than 30 minutes. Usually, loss of consciousness is very brief and ranges between a few seconds to minutes. Mild TBI remains the biggest percentage of all closed head, brain injury cases admitted to the hospitals. Currently, the primary criterion for evaluating patients with TBI in clinical setting is the Glasgow Coma Scale (GCS), which assesses the level of consciousness following TBI. A mild traumatic brain injury is most likely to be diagnosed only when there is a change in the mental status at the time of injury or hospital admission (the person is dazed, confused, or loses consciousness, GCS score 13-15). In US 10% of head injury patients are classified at admission as having severe (GSC below 8), 10% as moderate (GCS 9-12), and remaining 80% as mild TBI (GCS 13-15) (Narayan R K, Michel M E, et al, J Neurotrauma., 2002). Similar proportions are indicated by World Health Organization in Europe, that estimated 70 to 90% of treated head injuries are classified to present as mild (Cassidy J D et al, 2004, Journal of Rehabilitation Medicine). It remains a public health problem as 10% of patients with mTBI can suffer long-term disabilities such as headache, fatigue, difficulty thinking, memory problems, attention deficits, mood swings, sleep disorders, frustration and even epileptic events (Jallo and Narayan, 2000; Narayan et al, 2002). Due to the complicated etiology it remains challenging to identify which patients with mTBI can be safely sent home without the need for treatment intervention (Jagoda et al., 2008). Currently to counter-act possible post-traumatic complications and secondary brain damages mTBI patients are further diagnosed with tools such as computerized tomography (CT) scans and magnetic resonance imaging (where available) (Graham et al., 1998). In the group of patients with mTBI only 3 to 19% present with an abnormal CT result revealing an acute intracranial lesion in patients (Jagoda et al., 2008; Bazarian et al., 2006; Borg et al., 2004). The other 80%+ of these scans show normal head CT, indicating no complications from injury, and as such are not cost effective and are time-consuming for both patient and medical staff.

The use of biomarkers has been proposed as a means to reduce the amount of unnecessary CT scans (Berger et al. 2007; Poli-de-Figueiredo et al., 2006) and for use in decentralized sites where access to CT equipment is absent. However so far no biomarker-assay is available which gives test results capable of properly classifying the majority of patients and therefore useful in serial screening.

As described the method of choice today is a CT scan due to the insufficient reliability and high percentage of false negative results with known biomarkers for TBI detection. One such known biomarker is S100B.

In recent years, S100B has been extensively investigated as a potential promising blood marker for mTBI (Ruan S et al., 2009; Goyal et al. 2013). Nevertheless, its clinical utility remains controversial. In mTBI adults, S100B below a cut-off of 0.1 µg/L was described to allow a maximal reduction of 30% in CT scans (ref from researchers). S100B failed to be a relevant prognostic marker for pediatric TBI patients, estimated only as adjunct in determining children with low-risk TBI (Tavarez et al., 2012; Filippidis et al., 2010).

S100B is a low-molecular-weight (9-13 kDa), non-ubiquitous $Ca^{2+}$-modulated protein implicated in e.g. regulation of enzyme activities, dynamics of cytoskeleton elements, cell growth and differentiation and $Ca^{2+}$ homeostasis (Donato R., 2003). In the central nervous system (CNS) it is primarily found and secreted by glial cells (Donato R., 2003). Due to its involvement in calcium homeostasis it has neuroprotective function e.g. prevents mitochondrial failure and cell death in the absence of glucose by increasing cellular calcium concentrations (Bargeror et al, 1995) or promote neurite outgrowth and astrocytic proliferation (Reeves et al, 1994). Significantly increased S100B levels are associated with severe TBI and may reflect ongoing structural damage and cell death after injury (Ingebrigtsen et al. 2002, Missler et al, 1999).

In an injury like mTBI one cannot risk a significant percentage of false negatives in view of the detrimental consequences if a patient exhibiting mTBI would be allowed to leave the hospital and suffer serious complications, or even death thereafter due to a wrong diagnosis. Thus the cut-offs defined for such tests need to be biased towards very high specificity (close to 100%) which can result in a very low sensitivity in consequence. This limitation has made the known individual biomarkers for mTBI not feasible for routine diagnostics in a clinical setup.

In view of the cost pressure in healthcare and the high cost of a CT scan it is highly desirable and a long felt need to find alternative, reliable and cost-effective routes of classifying a potential mTBI patient.

Thus one object underlying the present application is to provide for alternative or new feasible biomarkers for the detection or/and classifying of any brain related traumatic state and in particular for mTBI, and for assays and devices useful and reliable therefore and in mTBI diagnostics which can be used in a clinical or non-clinical context, or to improve known approaches to neurological or mTBI screening and analysis.

SUMMARY OF THE INVENTION

In one aspect the invention provides a method, composition, kit, assay for the classifying or detection of brain injuries or disorders or diseases like TBI, transient ischemic attack, brain tumors, seizures, epilepsia, cerebral abscess, encephalopathies and multiple sclerosis by use of a combination of markers like glutathione S transferase Pi (GSTP), fatty-acid-binding protein (FABP), glial fibrillary acidic protein (GFAP), neuron-specific enolase (NSE), neuromodulin (GAP43), neurofilament protein H (NFH), neurofilament protein M (NFM), neurofilament protein L (NFL), S100B, Tau, spectrin breakdown products, ubiquitin carboxyl terminal hydrolase-L1 (UCH-L1), vascular cell adhesion protein 1 (VCAM), serum amyloid A (SAA), Chemokine (C-C motif) ligand 23 (CCL23), peroxiredoxin 1 to 6 and nucleoside diphosphate kinase (NDKA).

In another aspect the present invention provides a combination of a selection of blood brain biomarkers (GSTP1, H-FABP, VCAM, NDKA) optionally combined to the known (and not sufficiently specific) S100B for reliable detection of brain injury like a disease or disorder selected from the group consisting of TBI, transient ischemic attack, brain tumors, seizures, epilepsia, cerebral abscess, encephalopathies and multiple sclerosis in a sample and in particular for mTBI detection. In particular these biomarkers were combined and adjusted in panels yielding specificity above 50% at a fixed sensitivity of 95% or 100%. This will allow clinicians and also on site medical emergency staff to better manage the detected diseases or disorders and in particular mild TBI patients and therefore potentially reduce CT scans but also the consequences associated with a delayed diagnosis of brain injury.

In another aspect the invention concerns devices, e.g. biomarker panels, to detect early traumatic brain injury (TBI) lesions better or complement S100B to rule out CT scans in mild TBI patients.

In other aspects the invention relates to methods and devices for the detection of a medical condition in a patient like TBI and mTBI.

In another aspect the invention relates to a method and devices making use of an algorithm to detect a medical condition of an individual in a sample.

In another aspect the invention relates to methods of treating an individual or patient diagnosed with a TBI or mTBI using such biomarkers.

DETAILED DESCRIPTION OF THE INVENTION

The invention relates to a method for screening for a disease or disorder selected from the group consisting of TBI, transient ischemic attack, brain tumors, seizures, epilepsia, cerebral abscess, encephalopathies and multiple sclerosis in a specimen (sample) comprising the steps of using a sample under suitable conditions and detecting at least two biomarkers under suitable conditions wherein the biomarkers are selected from the group consisting of glutathione S transferase Pi (GSTP), fatty-acid-binding protein (FABP), glial fibrillary acidic protein (GFAP), neuron-specific enolase (NSE), neuromodulin (GAP43), neurofilament protein H (NFH), neurofilament protein M (NFM), neurofilament protein L (NFL), S100B, Tau, spectrin breakdown products, ubiquitin carboxyl terminal hydrolase-L1 (UCH-L1), vascular cell adhesion protein 1 (VCAM), serum amyloid A (SAA), Chemokine (C-C motif) ligand 23 (CCL23), peroxiredoxin 1 to 6 and nucleoside diphosphate kinase (NDKA).

The invention has the potential to make a world broad impact on the clinical practice in the management of brain injuries and in particular mTBI. The invention is feasible to provide for a diagnostic panel of markers that can be easily used and are reliable and safe.

The results described below on S100B, GSTP, NDKA, VCAM and H-FABP panels of at least two of these molecules highlight that a point of care test (POCT) or an array can be readily used for diagnostic purposes. Traumatic brain injury (TBI) is the leading cause of death and disability in adults younger than 40 years and in children worldwide. Accurate determination of the initial brain damage after brain injury is crucial in establishing a neurologic prognosis and to balance risks and benefits of treatment options. The invention advantageously provides for such a tool and method.

In a preferred embodiment the invention relates to a method wherein the biomarkers are selected from S100B, GSTP, HFABP, VCAM and NDKA or fragments, variants or mutants thereof. Particularly useful is the combination of two or three markers.

Unexpectedly and surprisingly the inventors could show that by a combination of at least two markers of the invention a reliable and easy to use method can be provided to reliably analyse a specimen and thereby rule out brain injury complications in an individual characterized by mTBI and thereby to avoid costly CT scans or even transportation to a centre capable of performing such.

It was not predictable that the markers of the invention and the particular selection of certain markers or/and the combination of certain markers could be applied to provide for a reliable and specific method to assay for the brain injuries or disorders or diseases or medical complications as described herein and particularly TBI and mTBI. The invention will have not only a positive impact on cost in such analysis and specifically mTBI analysis but represents also an easy to use and fast method in this medical area.

In particularly the invention is advantageous in that it provides for an improved specificity (>50%) for 100% sensitivity to rule out CT scans in brain injuries or other complications and mild TBI patients using a panel of at least two markers within S100B, GSTP, HFABP, VCAM and NDKA.

A direct comparison of available state of the art markers with the invention makes it apparent how advantageous the invention is: with a panel of 3 new biomarkers according to a preferred embodiment of the invention, whereby sensitivity is 100%, 58% of the mTBI could be directly discharged compared with 34% for individual S100B marker analysis.

Another advantageous embodiment is a combination with the molecule markers as described herein with other markers like age or GCS. In particular such an application and use of the markers according to the invention in a particular patient group characterized by GCS score of 13 or more or 15 or more, or in a particular age group, e.g. 60 years or more, 65 years or more, 70 years or more will yield very positive and highly reliable test results. More so, in this manner the invention positively achieves that reliable test results can be achieved by the use of less molecular markers which does not only have technical advantages but is also advantageous from a cost point of view.

The invention provides the unexpected advantage that a brain injury and the particular medical complications as described herein can be identified and screened for not only in a fully equipped hospital but by use of a simple test device anywhere and without the use of qualified medical personnel.

In the following certain terms of the invention will be defined in more detail.

"Brain injury" is any state of a patient or individual which is the cause of sudden impact on the head or the individual. A particular brain injury is TBI or mTBI.

"TBI" in the sense of the invention is any brain injury caused by a traumatic incident as described above with reference to the prior art.

"Identification" or "identify" or "classify" in the sense of the invention is the analysis of a sample of an individual to assess whether the individual has a brain injury and particularly TBI or mTBI; the identification of e.g. TBI and mTBI can be verified by use of a CT scan or MRI analysis.

"Diagnostic method" or "diagnostic" in the sense of the invention is any useful method with a suitable sequence of method steps for the detection, visualization and/or quantification of the test result generally known in the art.

"Assay" in the sense of the invention is any method generally known in the art to detect TBI or mTBI like ELISA or any other standard methods for detection of biomarkers.

"Device" in the sense of the invention is a combination of the biomarkers or panel of biomarkers according to the invention that can be used to perform an assay for TBI or mTBI detection. Examples are carrier plates, test stripes, biochip arrays or the like known in the art.

"Marker" or "biomarker" or "molecular marker" or "molecular biomarker" in the sense of the invention is any useful biomarker to detect in a sample of preferably blood, plasma, saliva, tears, CSF or urine a brain injury, preferably traumatic brain injury (TBI) or other disorders as described below; preferably the combination of at least two markers is suitable to detect mild TBI (mTBI); the markers are used in a suitable assay setup wherein preferably the selectivity is set to 100% and the specificity is preferably more than 40%, even more preferred more than 50%, more than 55%, more than 58%, 60% or 70%.

As a marker in the sense of the invention qualifies any marker of glial cells, neuronal cells, or vascular cells. Preferred markers of the invention are:
  Glutathione S Transferase Pi (GSTP)
  Fatty-acid-binding protein (FABP)
  Glial fibrillary acidic protein (GFAP)
  Neuron-specific enolase (NSE)
  Neuromodulin (GAP43)
  Neurofilament protein H (NFH)
  Neurofilament protein M (NFM)
  Neurofilament protein L (NFL)
  S100B
  TAU
  Nucleoside diphosphate kinase (NDKA)
  Spectrin breakdown products
  Ubiquitin carboxyl terminal hydrolase-L1 (UCH-L1)
  Vascular cell adhesion protein-1 (VCAM)
  Serum amyloid A (SAA)
  Chemokine (C-C motif) ligand 23 (CCL23)
  Peroxiredoxin 1 to 6

In addition to the "markers" as described above it is also within the scope of the invention that one, two, three or even more markers can be combined with defining the patient or individual by age or GCS score. Age and GCS can thus be denoted as "marker" in the sense of the invention. Such markers like age and GCS can also be used in the sense of the invention to define a patient subgroup or subgroup of individuals. A preferred age group is below 50, 60, 70 or more than 50, 60, 65, 70 years of age. A GCS of 13 to 15 can preferably be used to define a patient subgroup and can be used in combination with any of the other markers defined herein. In such a manner the individuals can be stratified and patient groups can be formed both to adapt and increase the test performance or to reduce the markers needed to achieve a reliable test result and preferably to adjust the features of the detection method or the components of a test kit.

A marker "panel" in the sense of the invention is a combination of at least two biomarkers, preferably two or three markers, used in combination in a suitable setup or device.

"Sensitivity" in the sense of the invention refers to the assay result of true positives in the analysis of TBI or mTBI. Preferably the sensitivity in the analysis according to the invention is set to 95% to 100%, or 100% (i.e. no false negative diagnoses).

"Specificity" in the sense of the invention is the so-called true negative rate in an assay to identify TBI or mTBI. The specificity is preferably targeted to be at least 50% and preferably higher, e.g. 58%, 60%, 65%, 70%.

A "sample" or "specimen" in the sense of the invention is any fluid or tissue useful for performing an assay or detection method to identify TBI, preferably mTBI. Preferably the sample is a blood, plasma or urine sample taken from an individual. The sample is treated according to generally known procedures to keep or make them feasible for the marker analysis according to the invention.

In the following preferred embodiments of the invention will be described.

In a preferred embodiment the invention relates to a method wherein the sample is blood, plasma, saliva, tears, CSF, or urine. A blood sample is a very easy way of sample collection and thus the method according to the invention will be readily performed with simple means.

The method according to the invention can be applied to all disorders, diseases or medical complications as described herein and is particularly useful for TBI and in particular for mild TBI (mTBI).

In an alternative embodiment the invention concerns a composition comprising or consisting of at least two markers useful for TBI detection in a sample of an individual wherein the markers are selected from the group consisting of glutathione S transferase Pi (GSTP), fatty-acid-binding protein (FABP), glial fibrillary acidic protein (GFAP), neuron-specific enolase (NSE), neuromodulin (GAP43), neurofilament protein H (NFH), neurofilament protein M (NFM), neurofilament protein L (NFL), S100B, Tau, spectrin breakdown products, ubiquitin carboxyl terminal hydrolase-L1 (UCH-L1), vascular cell adhesion protein 1 (VCAM), serum amyloid A (SAA), Chemokine (C-C motif) ligand 23 (CCL23), peroxiredoxin 1 to 6 and nucleoside diphosphate kinase (NDKA).

Said composition advantageously is comprising or consisting of two or three markers wherein the markers are selected from S100B, GSTP, HFABP, VCAM and NDKA or fragments, variants or mutants thereof.

In an alternative embodiment the invention relates to a kit comprising or consisting of two or three markers of any of the above markers.

Furthermore, the invention relates to an assay device comprising or consisting of two or three markers of any of the above markers. Preferably the Assay device comprises or consists of a biochip, biomarker panel on a carrier, or test strip.

In addition to the above described embodiments it will be possible to combine the method and device of the invention with non-marker observations on the patient as part of a decision matrix, e.g. brain injury score, pupilar dilation, cognitive tests etc. which will lead to a reliable decision making of hospitalization of an individual or liberating him.

The invention encompasses also further subgroups of marker combinations being advantageous in terms of the test results that can be achieved. These subgroups are a combination of two, three, four or five markers selected from the group consisting of GSTP, FABP, GFAP, NSE, GAP43, NFH, NFM, NFL, S100B, VCAM, SAA, CCL23, peroxiredoxin 1 to 6 and NDKA. In particular preferred is a combination of two or three markers of GSTP, FABP, GFAP, NSE, GAP43, NFH, NFM, NFL, S100B, VCAM, SAA, CCL23, peroxiredoxin 1 to 6 and NDKA, more preferably a combination of S100B, VCAM and H-FABP, or GSTP, VCAM and H-FABP, or GSTP, FABP and GFAP, or SAA, VCAM and H-FABP, or peroxiredoxin 1, VCAM and H-FABP, or CCL23, VCAM and H-FABP, or S100B, VCAM and CCL23, or S100B, CCL23 and H-FABP, or NSE, GAP43 and NFH, or NFM, NFL and S100B, or FABP, GFAP and NSE, or GAP43, NFH and NFM, or NFL, S100B and NDKA, or GAP43, NFH and NFM, or NFL, S100B and NDKA, or GFAP, NSE and GAP43, or NFH, NFM and NFL.

The invention will be described in more detail in the following examples which are meant to be illustrative without any restriction and which represent preferred embodiments of the invention.

As will be apparent from the experimental part describing the invention, the invention has the advantage that it achieves very reliable test results. Accordingly in preferred embodiments it provides for a method, composition, kit or assay wherein the sensitivity is more than 95%, preferably 100%, and the specificity is more than 50%, preferably more than 55%, more preferably more than 60%, and more preferably more than 70%.

In an alternative embodiment the invention provides for a method of or a system for analyzing in a specimen a medical condition wherein a medical device as described herein is applied under appropriate conditions, making use of any of the biomarkers described herein for the analysis of any of the disorders or diseases of the invention and making use of an algorithm wherein the test results are further defined by way of the algorithm, e.g. quantified.

The steps of such a method or system are in a preferred embodiment as follows:

The method and system are capable to analyze at least two test results in a sample of an individual, useful for the diagnosis of a medical condition like brain injury, with the system comprising:

(a) at least two databases comprising:
  (i) a first test result collected from a first diagnostic test;
  (ii) a second test result collected from a second diagnostic test different than the first diagnostic test;
  (iii) optionally, subsequent test result(s) collected from subsequent diagnostic test(s) different from the previous diagnostic test(s);
  (iv) optionally, secondary subject observations or measurements;
  (v) one or more diagnostic cut-offs associated with the first diagnostic test, with the second diagnostic test, with subsequent diagnostic tests, and with the subject observations or measurements, wherein such cut-offs collectively integrate to assess probability of brain injury status.

(b) one or more processors operatively encoded to automatically:
  (i) apply an interpretation algorithm to generate a subject result coordinate based on the database of test results;

(ii) optionally apply a second interpretation algorithm to generate a probability of error in the subject result coordinate.

In another alternative embodiment, methods of treatment of an individual or patient diagnosed with a TBI or mTBI using the biomarkers or biomarker combinations disclosed herein are contemplated. Any known method of treatment capable of treating a TBI or mTBI may be used to treat the patient or individual once diagnosed using the biomarkers or biomarker combinations disclosed herein. Due to the complex etiology of TBI, treatments widely vary and depend on the characteristics and severity of the injury. In some embodiments, the TBI is treated with one or more pain reliving agents, one or more anti-seizure agents, one or more coma-inducing agents, one or more diuretic agents, one or more anti-anxiety agents, one or more anti-depressive agents, one or more hyperosmolar therapies, one or more cognitive therapies, one or more rehabilitation therapies including physical, occupational, and speech therapies, one or more therapeutic hypothermia therapies, one ore more stem cell therapies, one or more surgical therapies, rest, head elevation, hyperventilation, or combinations therof. In a specific embodiment, the TBI is a TBI lesion that is treated by surgery to remove the lesion. The biomarker panels disclosed herein surprisingly and unexpectedly detect TBI or mTBI with high specificity and sensitivity, resulting in better treatment decisions by medical personnel and outcomes.

EXAMPLES

The following examples are meant to illustrate the invention in more detail without to be construed as limiting in any sense.

Example 1

The blood GSTP1, H-FABP, NDKA, VCAM and S100B content of patients presenting or not cerebral lesions on CT scan with a Glasgow Coma Scale >13 and within 6 hours after the onset of TBI were quantified and compared using ELISA analysis. The study population comprised a total of 97 individuals.

ELISA was performed using 96-well homemade assays for GST-Pi and NDKA as described elsewhere (Turck, et al. 2012), H-FABP from Hycult (NL) and CCL23, SAA, peroxiredoxin 1 and S100B from Abnova (TW). Each plasma sample were assayed in duplicate and distributed randomly on the plates.

Protein levels were initially expressed in relative fluorescence unit (RFU) and concentrations were calculated using a calibration curve obtained on the same plate with the recombinant proteins. Statistical analyses were performed using IBM SPSS Statistics software version 19.0.0 (IBM Corporation, NY, USA). To assess the ability of proteins to discriminate between different populations, non-parametric tests were performed. A Wilcoxon matched pairs test was performed for age and sex matched data and a Mann-Whitney for non-matched data. For data containing more than two groups, a one-way ANOVA Kruskal-Wallis test was used. Receiver Operating Characteristic (ROC) curves analysis was performed and cut-off (CO) points obtained from the curves. Optimal threshold values were chosen to provide the highest specificity for 100% sensitivity. Multivariate logistic regression analysis was used to compare the values of plasma S100B, H-FABP, GST-Pi, VCAM, CCL23, SAA, peroxiredoxin 1 and NDKA levels as CT scan rule out markers.

In these experiments the inventors succeeded in providing a panel (i.e. a small set of two or three) of biomarkers or biomolecules that could be useful in a clinical setting. We could show that each member of the panel provides a different angle to the diagnosis and taken together they lead to a more accurate prediction. Each member of the panel fulfils several criteria: firstly it must have a predictive power itself, i.e. it must be able to distinguish the disease types to a certain extent. Secondly it must be easy to measure with high reproducibility. Thirdly, it should have a central role in the biological processes that were found by the network analysis.

S100B, H-FABP, GST-Pi, VCAM, CCL23, SAA, peroxiredoxin 1 and NDKA were identified as particularly useful in such a panel analysis according to the invention. We developed PanelomiX toolbox, which is able to extract optimal panels from a small number of molecules and provides a simple, easy to interpret set of threshold rules for disease type classification. The rule-based classifier just counts the number of molecules whose quantity passes specific threshold values. It mimics the way many clinical scores are built and is therefore easy to understand by people working in a clinical environment. Briefly, the optimized cut-off values were obtained by iterative permutation-response calculations using all available parameters. Each cut off value was changed iteratively by quantiles of 2% increment, and specificity was determined after each iteration until a maximum of specificity was achieved for 100% sensitivity.

Results Example 1

The figures as described above show the results of the specificity comparison of S100B alone vs. different panels of two or three molecules/biomarkers of the invention. The sensitivity has been set at 100%. It demonstrates that our cohort is comparable to all published mTBI cohorts analysing S100B. When sensitivity is set at 100%, a 37% of specificity is obtained. GSTP and HFAB have a specificity of 25%, NDKA of 12% and VCAM of 40%. This confirms all previous results on the limited capacity of S100B alone to rule-out negative CT patients and the need of additional parameters/biomarkers.

| Marker(s) | Sensitivity % | Specificity % |
| --- | --- | --- |
| S100B | 100 | 37 |
| GSTP | 100 | 25 |
| HFABP | 100 | 25 |
| NDKA | 100 | 12 |
| VCAM | 100 | 40 |
| SAA | 100 | |
| CCL23 | 100 | |
| Peroxiredoxin | 100 | |

When molecules are combined into panels of three molecules, the specificity increases up to 58% (S100B, HFABP and GSTP) and up to 49% when two molecules are combined (S100B and NDKA).

| Marker(s) | Sensitivity % | Specificity % |
| --- | --- | --- |
| S100B/HFABP/GSTP | 100 | 58 |
| S100B/HFABP/NDKA | 100 | 57 |
| GSTP/HFABP/NDKA | 100 | 51 |
| S100B/VCAM/HFABP | 100 | 60 |
| S100B/VCAM/SAA | 100 | 59 |

-continued

| Marker(s) | Sensitivity % | Specificity % |
|---|---|---|
| S100B/VCAM/CCL23 | 100 | 63 |
| S100B/VCAM/Perox 1 | 100 | 62 |
| S100B/NDKA | 100 | 49 |
| GSTP/HFABP | 100 | 43 |
| HFAB/VACM | 100 | 59 |
| S100B/VACM | 100 | 46 |
| S100B/CCL23 | 100 | 45 |
| HFABP/CCL23 | 100 | 48 |
| VCAM/CCL23 | 100 | 44 |

The results described here on S100B, GSTP, NDKA, VCAM, CCL23, SAA, peroxiredoxin 1 and H-FABP panels of at least two of these molecules or a combination of three as shown highlight that they can be easily used in a POCT or an array for serial diagnosis.

The combination of a least two out of GSTP1, H-FABP, VCAM, NDKA, CCL23, SAA, peroxiredoxin 1 and S100B in panels gives rise to increased specificity above 50% for a sensitivity of 100% to rule out CT scans in mild TBI patients.

Accordingly, the surprising and unexpected advantage is an improved specificity (>50%) for 100% sensitivity to rule out CT scans in mild TBI patients using a panel of two or three markers within S100B, GSTP, HFABP, VCAM, CCL23, SAA, peroxiredoxin 1 and NDKA.

The experimental results and the advantages of the invention are also apparent from the following tables:

|  | Sensitivity % | Specificity % | Sensitivity % | Specificity % |
|---|---|---|---|---|
| S100B | 100 | 37 | 95-100 | 37 |
| GSTP | 100 | 25 | 95-100 | 36 |
| HFABP | 100 | 25 | 95-100 | 25 |
| NDKA | 100 | 12 | 95-100 | 27 |
| VCAM | 100 | 40 | — | — |
| CCL23 | 100 | 25 | 95-100 | 23 |
| SAA | 100 | 23 | 95-100 | 20 |
| Peroxiredoxin 1 | 100 | 20 | 95-100 | 22 |

| Marker(s) | Sensitivity % | Specificity % | Sensitivity % | Specificity % |
|---|---|---|---|---|
| S100B/HFABP/GSTP | 100 | 58 | 95-100 | 61 |
| S100B/HFABP/NDKA | 100 | 57 | 95-100 | 60 |
| GSTP/HFABP/NDKA | 100 | 51 | 95-100 | 52 |
| S100B/GSTP/Age | — | — | 95-100 | 64 |

| Marker(s) | Sensitivity % | Specificity % | Sensitivity % | Specificity % |
|---|---|---|---|---|
| S100B/NDKA | 100 | 49 | — | — |
| S100B/HFABP |  |  | 95-100 | 52 |
| GSTP/HFABP | 100 | 43 | 95-100 | 49 |
| HFABP/VACM | 100 | 59 | 95-100 | 62 |

Results in a patient group which includes only patients with an age of above 61 years are depicted in the following:

| | Sensitivity % | Specificity % | Sensitivity % | Specificity % |
|---|---|---|---|---|
| S100B/GSTP/Age | — | — | 95-100 | 64 |

It could also be shown that in said age group/patient population (i.e. patients above 61 years old) the best single biomarker is not anymore S00B but GSTP with a specificity of 50% as depicted below:

| | Sensitivity % | Specificity % | Sensitivity % | Specificity % |
|---|---|---|---|---|
| GSTP/Age | — | — | 95-100 | 50 |

Example 2

The blood H-FABP and GFAP content of patients presenting cerebral lesions or not on a CT scan were quantified and compared using ELISA analysis. The study population comprised a total of 25 individuals. The ELISA analysis was carried out in the same manner as in Example 1, above.

Demographic Characteristics of the Study Population

| | Ctrl (n = 15) | CT− (n = 24) | CT+ (n = 1) |
|---|---|---|---|
| Age, Mean (SD) | 40.67 (10.06) | 44.38 (14.76) | 44 |
| Sex (F) | 7 | 7 | 1 |
| HFABP POCT Median (IQR) | — | 3 (1.89-7.55) | 5.1 |
| GFAP MSD Median (IQR) | 39.47 (22.64) | 186.95 (52.32-711.15) | 38149 |

POCT = point-of-care testing kit
MSD = Meso Scale Diagnostics, LLC
IQR = interquartile range Results Example 2

Figure 1:
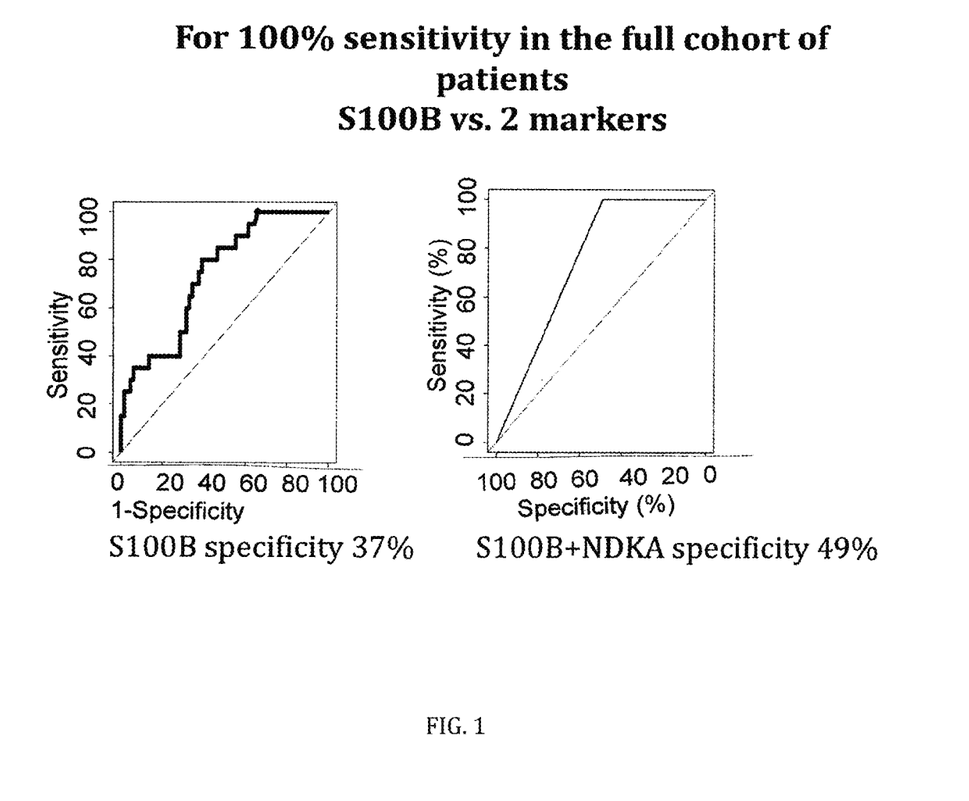
FIG. 1 shows a comparison of S100B (specificity 37%) and a combination of S100B+GSTP+HFABP (specificity 58%) for a 100% sensitivity in a cohort of mTBI patients. The invention thus can significantly improve the reliability of test results whereby it was not expected that said combination could provide for such an improvement and positive test results.
Figure 2:
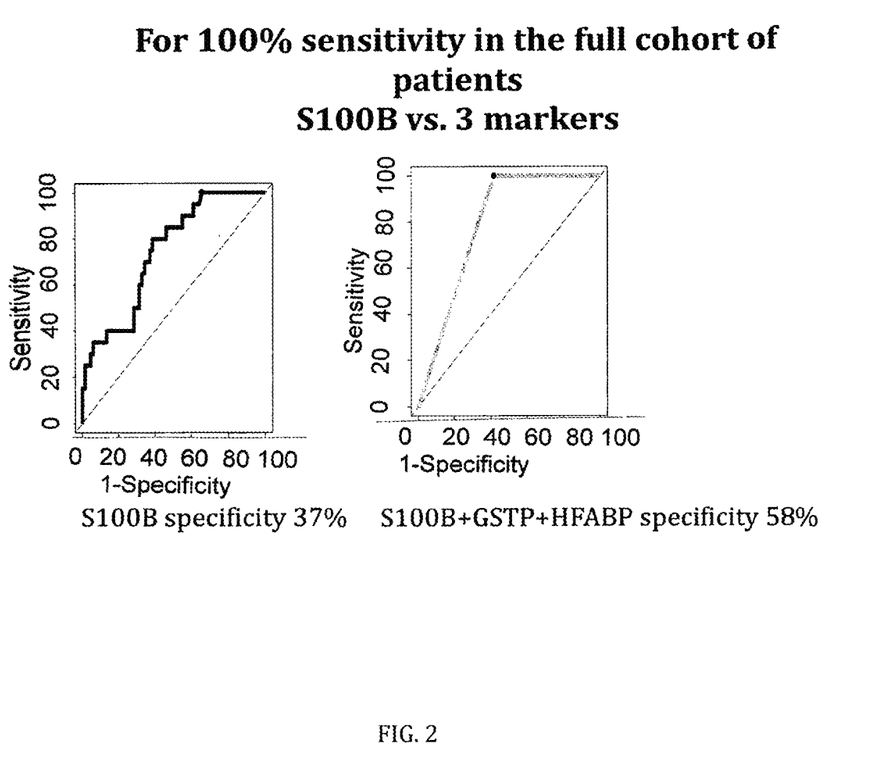
FIG. 2 shows a comparison of S100B (specificity 37%) and a combination of S100B+NDKA (specificity 49%) for a 100% sensitivity in a cohort of mTBI patients.
Figure 3:
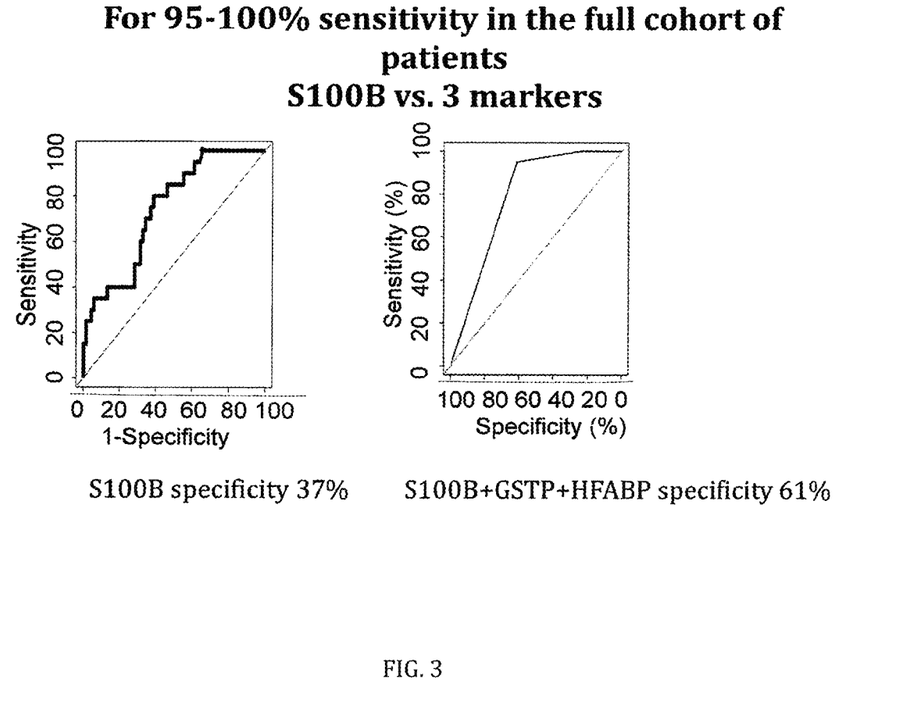
FIG. 3 shows a comparison of S100B (specificity 37%) and a combination of S100B+GSTP+HFABP (specificity 61%) for a 95-100% sensitivity in a cohort of mTBI patients.
Figure 4:
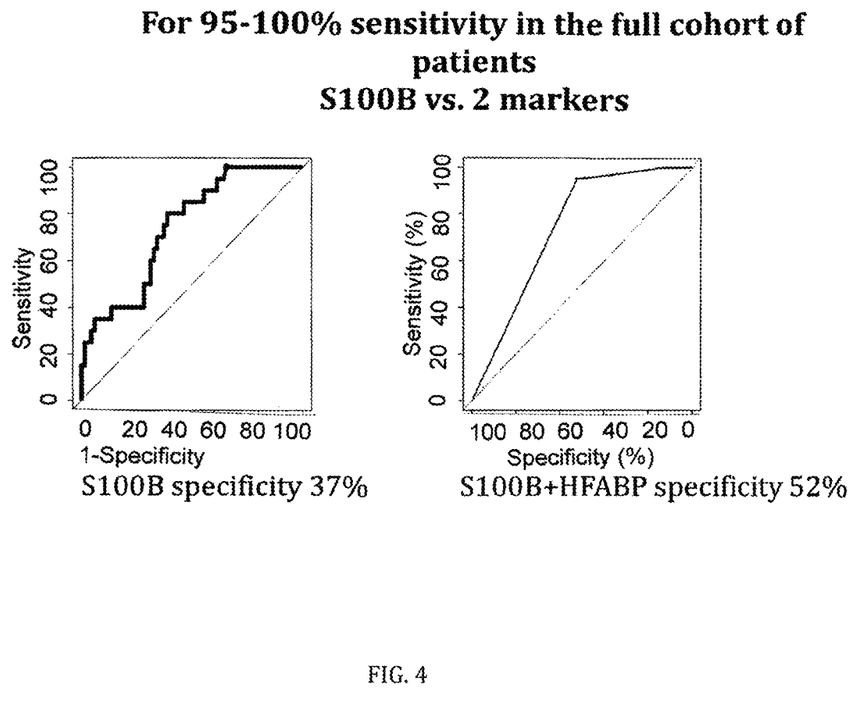
FIG. 4 shows a comparison of S100B (specificity 37%) and a combination of S100B+HFABP (specificity 52%) for a 95-100% sensitivity in a cohort of mTBI patients.
Figure 5:
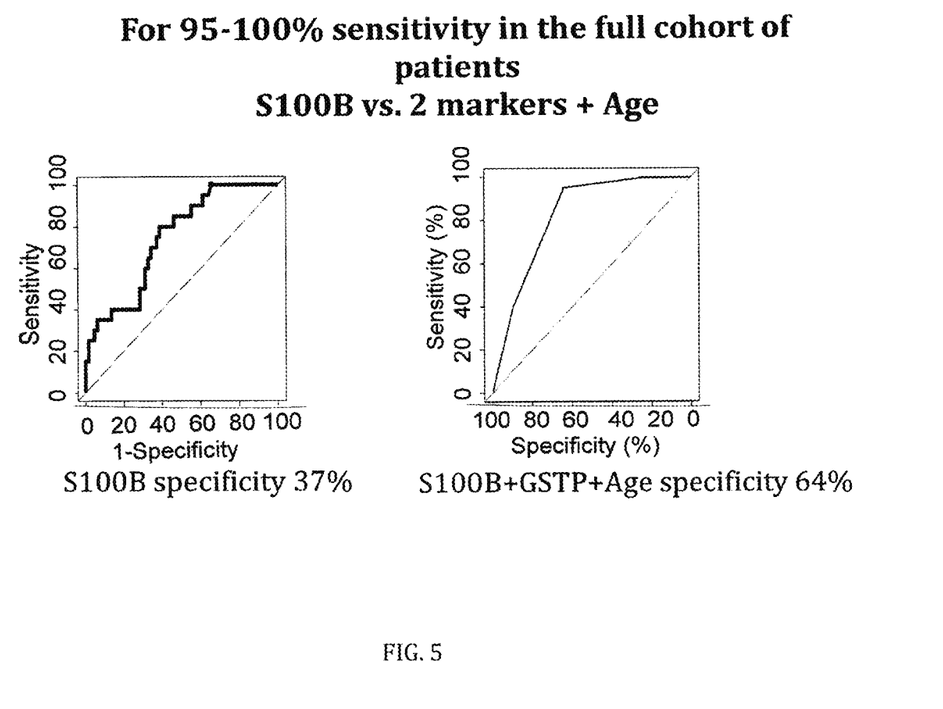
FIG. 5 shows a comparison of S100B (specificity 37%) in a full cohort and a combination of S100B+GSTP+Age (specificity 64%) for a 95-100% sensitivity in a cohort of mTBI patients. The age group in this case was defined in years.
Figure 6:
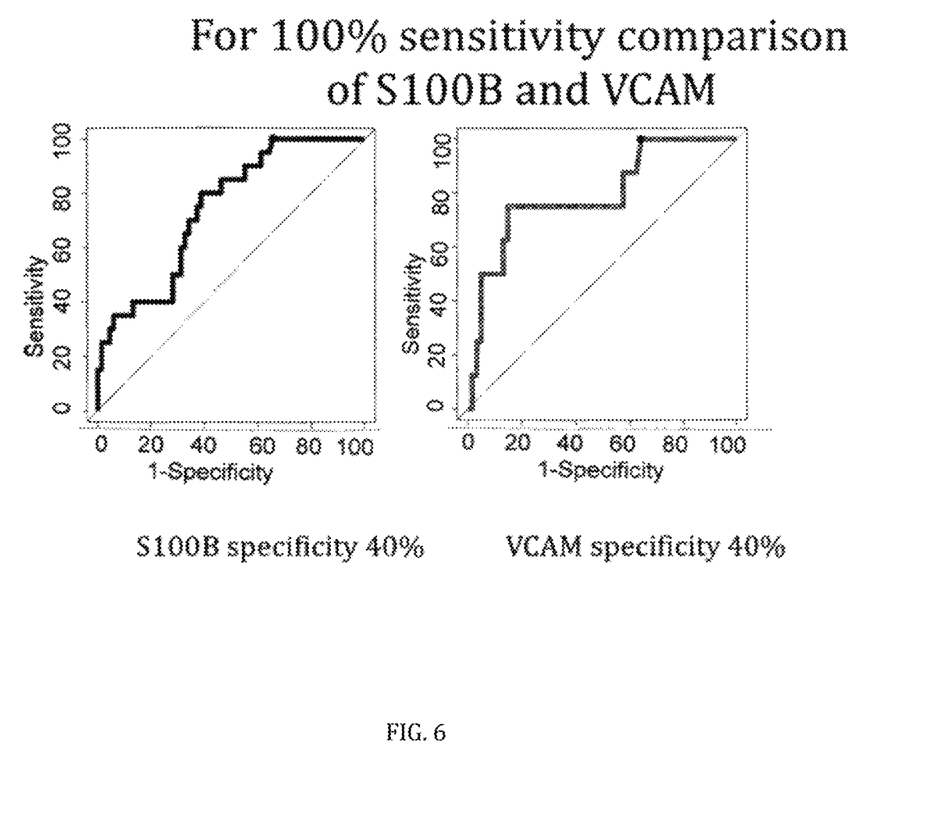
FIG. 6 shows a comparison of S100B (specificity 37%) and VCAM (specificity 40%) for a 100% sensitivity in a cohort of mTBI patients.
Figure 7:
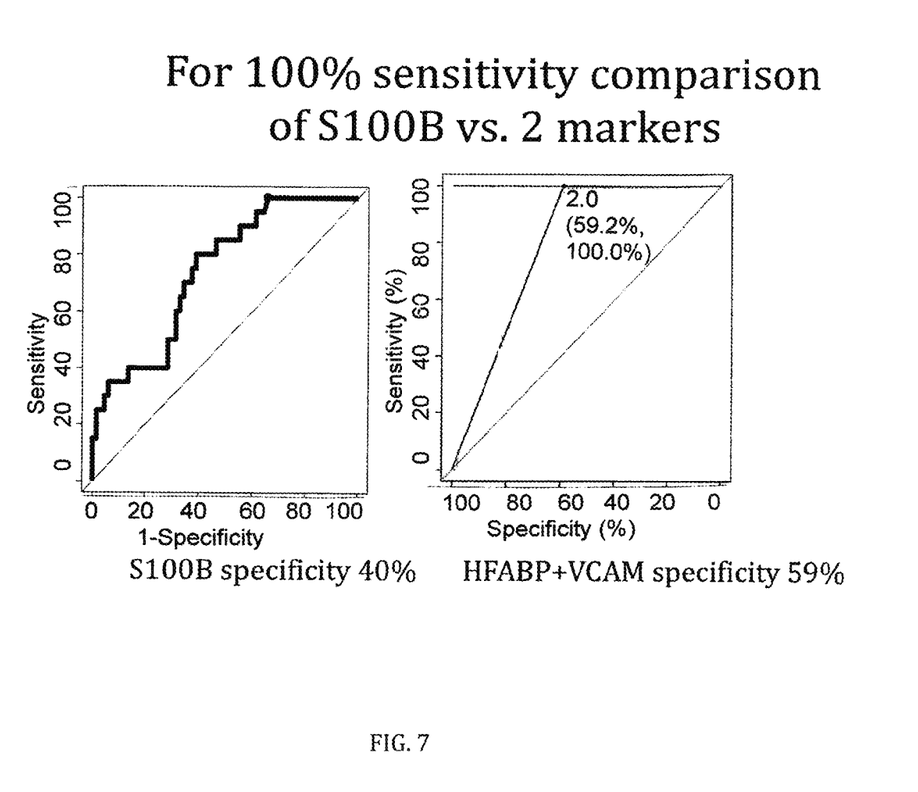
FIG. 7 shows a comparison of S100B (specificity 37%) and a combination of HFABP+VCAM (specificity 59%) for a 100% sensitivity in a cohort of mTBI patients. The scheme of FIG. 8 shows the advantage of using the biomarkers of the invention to avoid costly CT scans in a clinical setup.
Figure 8:
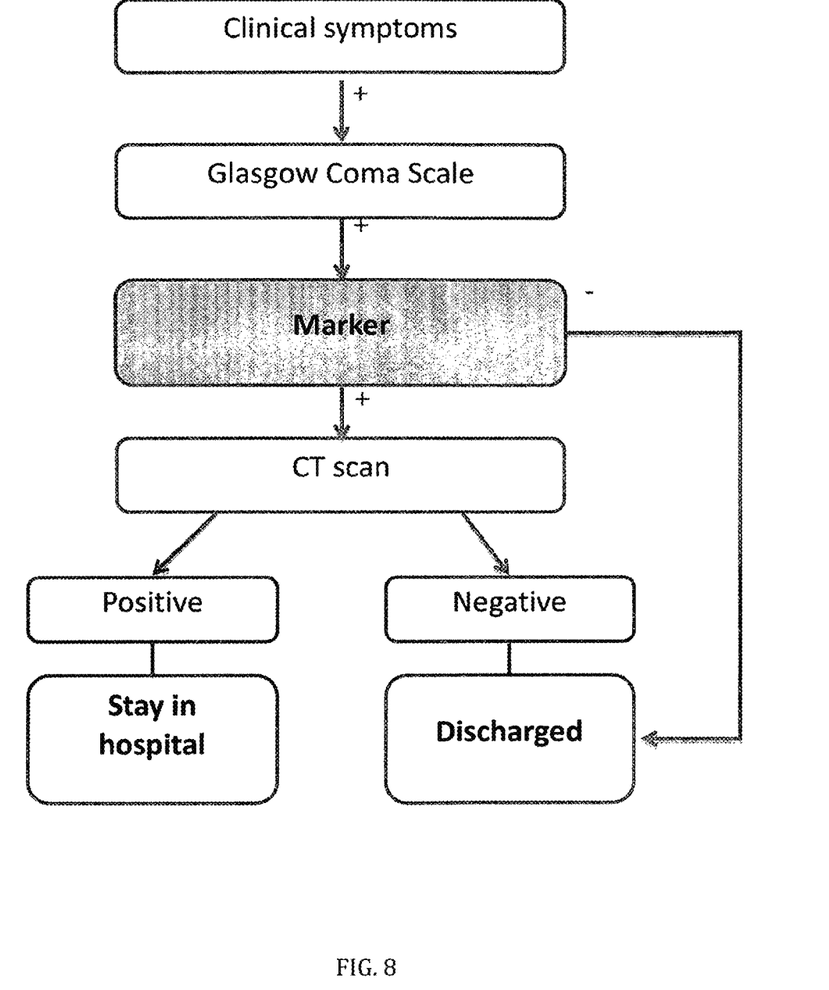
Figure 9:
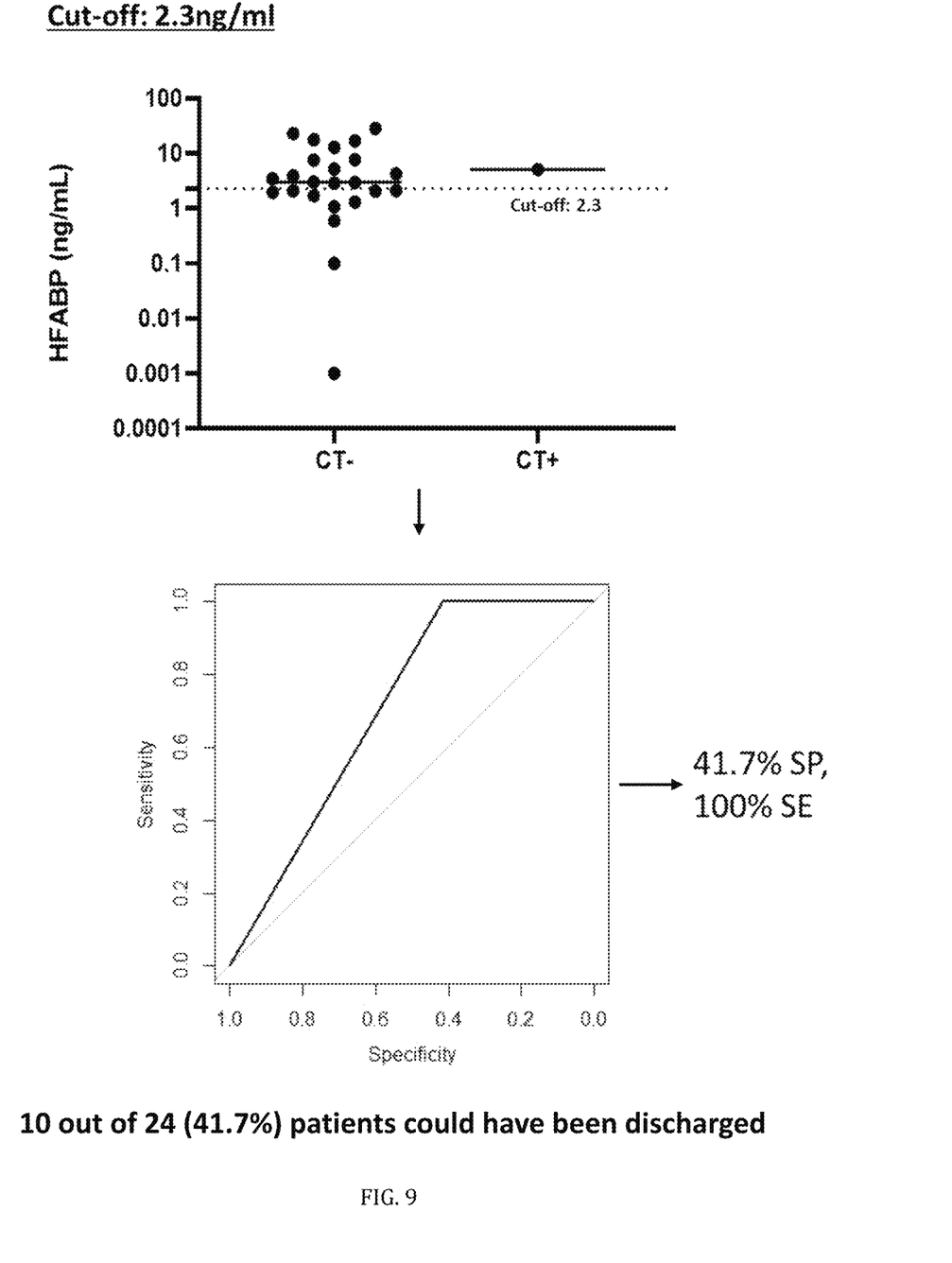
FIG. 9 shows data for HFABP (specificity 41.7%) for a 100% sensitivity in a cohort of mTBI patients.
Figure 10:
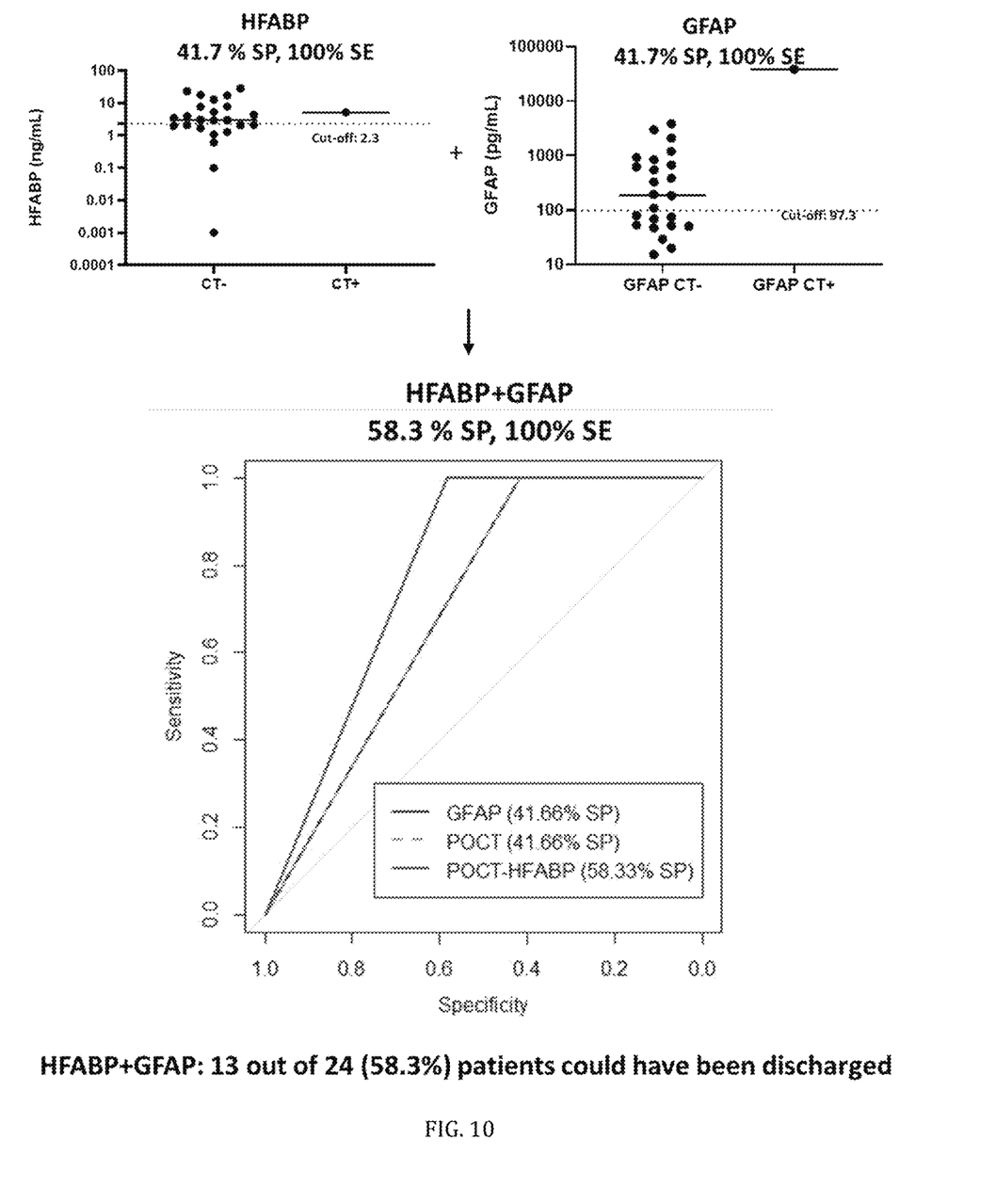
FIG. 10 shows a comparison of HFABP (specificity 41.7%) and a combination of HFABP+GFAP (specificity 58.3%) for a 100% sensitivity in a cohort of mTBI patients.

At a sensitivity of 100%, the specificity of the panel FABP/GFAP is increased if compared to the specificity of the two individual biomarkers. The cut-off values for FABP and GFAP were retrieved from Lagerstedt et al., PLOS One, 2018. These values amount to 2.3 (ng/ml) for HFABP and 97.3 pg/ml for GFAP. In FIG. 9, it is shown that, if considered a single biomarker (e.g., HFABP), a specificity of 41.7% can be obtained, corresponding to 10 of 24 patients with a CT negative outcome. If both HFABP and GFAP biomarkers levels are combined as show in FIG. 10, that is a patient is discharged if he or she shows at least one of the biomarker values below the corresponding cut-off, then the specificity increases to 58.3% corresponding to 14 of 24 patients with a CT negative outcome being discharged. Accordingly, this corresponds to a major improvement in the reliability of the diagnostic system to identify true CT positive and negative patients presenting cerebral lesions.

The invention claimed is:

1. A method of treatment of a disease or disorder, wherein the disease or disorder is a traumatic brain injury (TBI), the method comprising:
   a. obtaining a sample from the human patient;
   b. measuring a level of heart fatty-acid-binding protein (H-FABP) and a level of glial fibrillary acidic protein (GFAP) in the sample, and comparing the level of H-FABP and the level of GFAP to reference levels of H-FABP and GFAP to identify the patient as having the traumatic brain injury when the measured levels are higher than the reference levels; and c. administering a treatment to the patient;

wherein the treatment comprises one or more pain relieving agents, one or more anti-seizure agents, one or more coma-inducing agents, one or more diuretic agents, one or more anti-anxiety agents, one or more anti-depressive agents, one or more hyperosmolar therapies, one or more cognitive therapies, one or more rehabilitation therapies including physical, occupational, and speech therapies, one or more therapeutic hypothermia therapies, one or more stem cell therapies, one or more surgical therapies, rest, head elevation, hyperventilation, or combinations thereof.

2. The method of claim 1, wherein the disease or disorder is a mild traumatic brain injury (mTBI).

3. The method of claim 1, wherein the disease or disorder is a traumatic brain injury lesion.

4. The method of claim 3, wherein the treatment is surgery to remove the traumatic brain injury lesion.

5. The method of claim 1, wherein the age of the patient is below 50, 60, or 70 years of age.

6. The method of claim 1, wherein the age of the patient is more than 50, 60, 65, or 70 years of age.

7. The method of claim 1, wherein the sample is blood, plasma, urine, saliva, tears (lachrymal fluid), or cerebral spinal fluid (CSF).

8. The method of claim 7, wherein the sample is a blood sample.

\* \* \* \* \*

UNITED STATES PATENT AND TRADEMARK OFFICE
CERTIFICATE OF CORRECTION

PATENT NO. : 12,422,442 B2
APPLICATION NO. : 17/560297
DATED : September 23, 2025
INVENTOR(S) : Jean-Charles Sanchez and Joan Montaner Page 1 of 1

It is certified that error appears in the above-identified patent and that said Letters Patent is hereby corrected as shown below:

On the Title Page

Item (71) For the second applicant name, delete "RECERA" and insert --RECERCA--.

Signed and Sealed this
Ninth Day of December, 2025

John A. Squires
*Director of the United States Patent and Trademark Office*